United States Patent [19]

Kobrehel et al.

[11] Patent Number: 5,434,140
[45] Date of Patent: Jul. 18, 1995

[54] 9-DEOXO-9A-AZA-11-DEOXY-9A-HOMO-ERYTHROMYCIN A 9A,11-CYCLIC CARBAMATES

[75] Inventors: Gabrijela Kobrehel; Gorjana Lazarevski; Slobodan Djokic, all of Zagreb, Croatia

[73] Assignee: Pliva, farmaceutska, kemijska, prehranbena i kozmeticka industrija dionicko drustvo Zagreb, Zagreb, Croatia

[21] Appl. No.: 178,559

[22] Filed: Jan. 7, 1994

[30] Foreign Application Priority Data

Jan. 8, 1993 [HR] Croatia .................. P 93 0014 A

[51] Int. Cl.6 .................. A61K 31/70; C07H 17/08
[52] U.S. Cl. .................. 514/30; 514/29; 536/7.2; 536/7.4; 540/456
[58] Field of Search .................. 540/456; 536/7.2, 7.4; 514/29, 30

[56] References Cited

U.S. PATENT DOCUMENTS

| 4,328,334 | 5/1982 | Kobrehel et al. | 536/7.4 |
| 4,331,803 | 5/1982 | Watanabe et al. | 536/7.2 |
| 4,474,768 | 10/1984 | Bright | 536/7.4 |
| 4,492,688 | 1/1985 | Bright | 536/7.2 |

*Primary Examiner*—Cecilia Tsang
*Attorney, Agent, or Firm*—Pollock, Vande Sande & Priddy

[57] ABSTRACT

The invention relates to 9-deoxo-9a-aza-11-deoxy-9a-homoerythromycin A 9a,11-cyclic carbamates, novel semisynthetic macrolide antibiotics from the genus of azalides, of the formula (I)

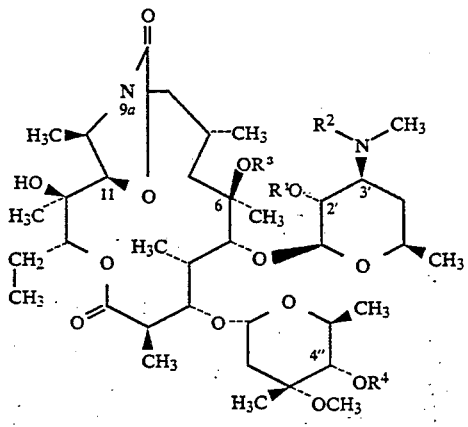

wherein

| $R^1=R^2=CO_2CH_2C_6H_5$, $R^3=R^4=CH_3$, | (IA) |
| $R^1=R^2=CO_2CH_2C_6H_5$, $R^3=CH_3$, $R^4=H$, | (IB) |
| $R^1=R^2=CO_2CH_2C_6H_5$, $R^3=R^4=H$, | (IC) |
| $R^1=R^2=H$, $R^3=R^4=CH_3$, | (ID) |
| $R^1=R^2=R^4=H$, $R^3=CH_3$, | (IE) |
| $R^1=R^2=R^3=R^4=H$, | (IF) |
| $R^1=H$, $R^2=R^3=R^4=CH_3$, | (IG) |
| $R^1=R^4=H$, $R^2=R^3=CH_3$, | (IH) |
| $R^1=R^3=R^4=H$, $R^2=CH_3$, | (IJ) | to pharmaceutically acceptable addition salts thereof with inorganic or organic acids, to intermediates and to processes for the preparation thereof, to a process for preparing pharmaceutical compositions as well as to the use of the obtained pharmaceutical compositions in treatment of bacterial infections.

26 Claims, No Drawings

9-DEOXO-9A-AZA-11-DEOXY-9A-HOMOERY- THROMYCIN A 9A,11-CYCLIC CARBAMATES

FIELD OF THE INVENTION

The invention relates to 9-deoxo-9a-aza-11-deoxy-9a-homoerythromycin A 9a,11-cyclic carbamates, novel semisynthetic macrolide antibiotics from the genus of azalides having antibacterial activity, of the general formula (I)

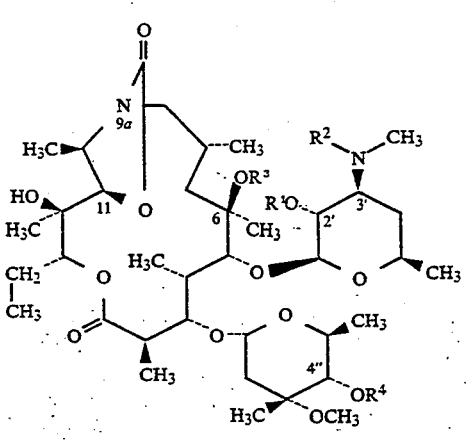

wherein

| | |
|---|---|
| $R^1=R^2=CO_2CH_2C_6H_5$, $R^3=R^4=CH_3$, | (IA) |
| $R^1=R^2=CO_2CH_2C_6H_5$, $R^3=CH_3$, $R^4=H$, | (IB) |
| $R^1=R^2=CO_2CH_2C_6H_5$, $R^3=R^4=H$, | (IC) |
| $R^1=R^2=H$, $R^3=R^4=CH_3$, | (ID) |
| $R^1=R^2=R^4=H$, $R^3=CH_3$, | (IE) |
| $R^1=R^2=R^3=R^4=H$, | (IF) |
| $R^1=H$, $R^2=R^3=R^4=CH_3$, | (IG) |
| $R^1=R^4=H$, $R^2=R^3=CH_3$, | (IH) |
| $R^1=R^3=R^4=H$, $R^2=CH_3$, | (IJ) | to pharmaceutically acceptable addition salts thereof with inorganic or organic acids, to intermediates and to processes for the preparation thereof, to a process for preparing pharmaceutical compositions as well as to the use of the obtained pharmaceutical compositions in the treatment of bacterial infections.

BACKGROUND OF THE INVENTION

Erythromycin A is a macrolide antibiotic, whose structure is characterized by a 14-member macrolactone ring with C-9 keto group. It was found by McGuire in 1952 (Antibiot. Chemother., 1952; 2:281) and for already 40 years it has been considered to be a sure and effective antimicrobial agent in the therapy of Gram-positive and some Gram-negative infections. However, in an acidic medium it is easily converted into anhydroerythromycin A, an inactive C-6/C-12 metabolite of a spiroketal structure (Kurath P. et al., Experientia 1971; 27:362). It is well known that the spirocyclization of the aglycone ring of erythromycin A is successfully inhibited by a chemical transformation of C-9 ketone or hydroxy groups in C-6 and/or C-12 position. By oximation of C-9 ketone (Djokic S. et al., Tetrahedron Lett., 1967; 1945) and by subsequent modification of the obtained 9(E)-oxime to 9-[O-(2-methoxyethoxy)-methyl-oxime-erythromycin methyl-oxime-erythromycin A (ROKSITROMICIN) (Ambrieres, G. S., FR 2,473,525 (1981)) or to 9(S)-erythromycylamin (Egan R. S. et al., J. Org. Chem., 1974; 39:2492) or its more complex oxazine derivative 9-deoxo-11-deoxy-9,11{imino[2-(2-methoxyethoxy)ethylidene]oxy}-9(S)-erythromycin A (DIRITROMICIN) (Lugar P. et al., J. Chryst. Mol. Struct., 1979; 9:329), there are synthetized novel semisynthetic macrolides, whose basic characteristics are, in addition to enhanced stability in an acidic medium, better pharmacokinetics and a long biological half-time with regard to the parent antibiotic erythromycin A. In a third way for modifying C-9 ketone, there are used Beckmann rearrangement of 9(E)-oxime and the reduction of the obtained imino ether (Kobrehel G. et al., U.S. Pat. No. 4,328,334, 5/1982) to 11-aza-10-deoxo-10-dihydroerythromycin A (9-deoxo-9a-aza-9a-homoerythromycin A) under broadening the 14-member ketolacton ring to 15-member azalactone ring. Reductive N-methylation of 9a-NH group according to Eschweiler-Clark process (Kobrehel G. et al., BE patent 892,357, 7/1982) or preliminary protection of an amino group under conversion to corresponding N-oxides and subsequent alkylation and reduction (Bright G. M., U.S. Pat. No. 4,474,768 10/1984) yield N-methyl-11-aza-10-deoxo-10-dihydroerythromycin A (9-deoxo-9a-methyl-9a-aza-9a-homoerythromycin A) (AZITROMICIN), a prototype of azalide antibiotics which are characterized, in addition to a broad antimicrobial spectrum including Gram-negative bacteria and intracellular microorganisms, by a specific transport mechanism to the application site, a long biological half-time and a short therapy period. EP A 0 316 128 (Bright G. M.) discloses novel 9a-allyl and 9a-propargyl derivatives of 9-deoxo-9a-aza-9a-homoerythromycin A and U.S. Pat. No. 4,492,688 (1/1985) to Bright G. M. discloses the synthesis and antibacterial activity of the corresponding cyclic ethers.

It is further well-known that intramolecular cyclization of the aglycone ring of erythromycin A is successfully inhibited by O-alkylation of C-6 hydroxy group. 6-O-methylerythromycin A (KLARITROMICIN) achieves, at a broad antimicrobial spectrum and stability in an acidic medium, high concentrations in serum and tissues (Watanabe Y. et at., U.S. Pat. No. 4,331,803, 5/1982).

EP A 0 467 331 (1/92; Kobrehel G. et al.) discloses the synthesis and activity spectrum of O-methyl derivatives of azithromycin.

SUMMARY OF THE INVENTION

As evident from the above, 9-deoxo-9a-aza-11-deoxy-9a-homoerythromycin A 9a,11-cyclic carbamates and pharmaceutically acceptable addition salts thereof with inorganic or organic acids, intermediates and processes for the preparation thereof as well as methods for the their preparation and use as pharmaceutical compositions have not been described as yet.

It has been found—and this represents an object of the present invention—that 9-deoxo-9a-aza-11-deoxy-9a-homoerythromycin A 9a,11-cyclic carbamates, novel semisynthetic macrolide antibiotics from the genus of azalides, and their pharmaceutically acceptable addition salts may be prepared by reacting 9-deoxo-9a- aza-9a-homoerythromycin A with benzyl chloroformate, O-methylating hydroxy groups in C-6 and/or C-4" position, deprotecting the protective groups and subsequently reductively N-methylating the 3'—NCH3 group and, if necessary, reacting the obtained compounds of the formula (I) with inorganic or organic acids.

DETAILED DESCRIPTION OF VARIOUS AND PREFERRED EMBODIMENTS

It has been found that 9-deoxo-9a-aza-11-deoxy-9a-homoerythromycin A 9a,11-cyclic carbamates of the formula (I)

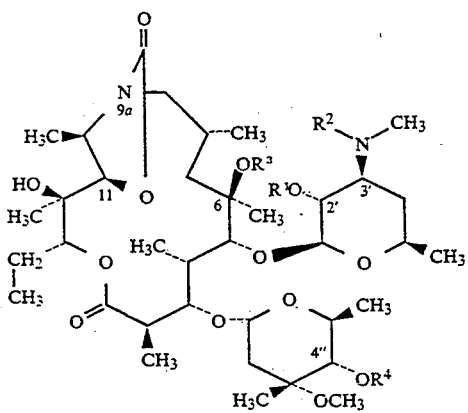

wherein

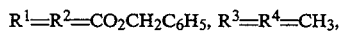  (IA)

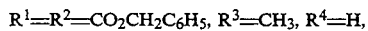  (IB)

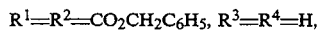  (IC)

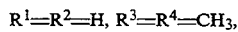  (ID)

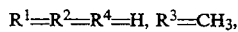  (IE)

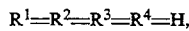  (IF)

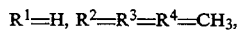  (IG)

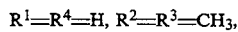  (IH)

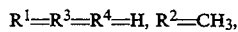  (IJ)

and pharmaceutically acceptable addition salts thereof with inorganic or organic acids may be prepared by the reaction of 9-deoxo-9a-aza-9a-homoerythromycin A of the formula (II)

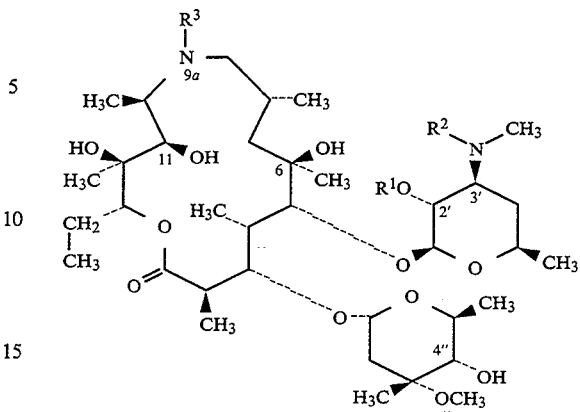

wherein

  (IIA)

with benzyl chloroformate in the presence of bases such as NaHCO3. The reaction is carried out in a solvent inert under the reaction conditions such as benzene or toluene. The reaction is carried out at a temperature of from room temperature to the reflux temperature of the solvent, for 3 hours to 3 days. O-methylation of the hydroxy groups in C-6 and/or C-4" position of the obtained 2'-O,(3',9a)-di-N-tris(benzyloxycarbonyl)-N-demethyl derivatives of the formula (II) is subsequently carried out, wherein

  (IIB)

The protective benzyloxycarbonyl group are eliminated and reductive N-methylation of the obtained 3'-N-demethyl derivatives with formaldehyde is carried out.

The above O-methylation of C-6 and/or C-4" hydroxy groups is carried out by the reaction of the compound of the formula (IIB) with 1 to 8 equivalents of the corresponding methylating agent in the presence of bases, in a polar aprotic solvent at a temperature from 0° C. to room temperature for 1 to 24 hours. Methyl iodide, dimethyl sulfate, methyl p-toluenesulfonate or methyl methanesulfonate may be used as the methylating agent. Although a relative excess of the methylating agent with regard to the compound (IIB) may be used, 1.2 to 2.4 equivalents with regard to the substrate are generally considered as sufficient. Inorganic hydrides such as potassium, sodium or lithium hydride, hydroxides such as potassium, sodium or lithium hydroxide, or organic bases such as n-butyllithium are used as appropriate bases. Polar aprotic solvents include dimethyl sulfoxide, N,N-dimethylformamide or a mixture thereof with solvents inert under reaction conditions such as tetrahydrofuran, 1,2-dimethoxyethane, acetonitrile or ethyl acetate. If necessary, further purification is carried out by chromatography on a silica gel column.

The thus obtained 9-deoxo-9a-aza-11-deoxy-9a-homoerythromycin A 9a,11-cyclic carbamates of the formula (I), wherein

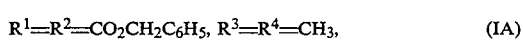  (IA)

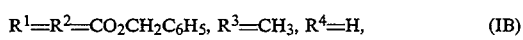  (IB)

  (IC)

are subjected, as a mixture or individually, to elimination of the protective benzyloxycarbonyl groups in 2'- and 3'-positions by hydrogenolysis process in solutions of lower alcohols such as ethanol, in the presence of sodium acetate/acetic acid buffer (pH 5) and a catalyst such as palladium black or palladium on carbon, in hydrogen atmosphere at a pressure of 1–20 bar under stirring at room temperature for 30 minutes to 10 hours. After filtering off the catalyst and evaporating the solvent, the product is isolated from water by extraction with hydrophobic solvents (pH 8–10.5) such as dichloromethane, chloroform, and/or ethyl acetate among others. If necessary, Further purification of the product is carried out by chromatography on a silica gel column to give TLC homogenous 3'-N-demethyl 9a,11-cyclic carbamates of the formula (I), wherein

$R^1=R^2=H, R^3=R^4=CH_3$, (ID)

$R^1=R^2=R^4=H, R^3=CH_3$, (IE)

$R^1=R^2=R^3=R^4=H$. (IF)

The obtained 3'-N-demethyl-9-deoxo-9a-aza-11-deoxy-9a-homoerythromycin A 9a,11-cyclic carbamates (ID)–(IF) are then subjected to reductive N-methylation with 1-3 equivalents of formaldehyde (37%) and with the same or a 2-fold amount of formic acid (98–100%) in a solvent inert under reaction conditions such as halogenated hydrocarbons, alcohols or lower ketones, at the reflux temperature of the reaction mixture, from 2 to 8 hours. The N-Page methylation produces 9-deoxo-9a-aza-11-deoxy-9a-homoerythromycin A 9a,11-cyclic carbamates of the formula (I), wherein

$R^1=H, R^2=R^3=R^4=CH_3$, (IG)

$R^1=R^4=H, R^2=R^3=CH_3$, (IH)

$R^1=R^3=R^4=H, R^2=CH_3$, (IJ)

which, if necessary, are subjected to chromatography on silica gel column or isolated by crystallization in a conventional way.

Pharmaceutically acceptable addition salts, which are also an object of the present invention, are obtained by reacting 9-deoxo-9a-aza-11-deoxy-9a-homoerythromycin A 9a,11-cyclic carbamates of the formula (I) with an at least equimolar amount of the corresponding inorganic or organic acid, such as hydrochloric acid, hydroiodic acid sulfuric acid, phosphoric acid, acetic acid, trifluoroacetic acid, propionic acid, benzoic acid, benzenesulfonic acid, methanesulfonic acid, laurylsulfonic acid, stearic acid, palmitic acid, succinic acid, ethyl succinic acid, lactobionic acid, oxalic acid, and/or salicylic acid, among others in a solvent inert under the reaction conditions. Addition salts are isolated by evaporation of the solvent or, alternatively, by filtration after spontaneous precipitation or by precipitation with the addition of a non-polar co-solvent.

9a,11-cyclic carbamates of the formula (I) and pharmaceutically acceptable salts thereof with inorganic or organic acids have a potent antibacterial activity. In vitro activity thereof is evidenced by tests on standard and freshly isolated microorganisms using Mueller-Hinton medium and the common method of a 2-fold dilution. Accordingly, they may be used as therapeutical agents in the treatment of infective diseases in humans and animals caused by different Gram-positive bacteria, mycoplasmas or generally patogenous organisms which are susceptible to compounds of the formula (I). To this purpose, the above compounds or pharmaceutically acceptable salts thereof with acids may be used orally in conventional daily doses from 0.2 to about 250 mg/kg of body weight, preferably from 5–50 mg/kg/day, or parenterally in the form of subcutaneous or intramuscular injections.

A process for preparing 9-deoxo-9a-aza-11-deoxy-9a-homoerythromycin A 9a,11-cyclic carbamates of the present invention is illustrated by the following Examples, which in no way should be construed as a limitation thereof.

EXAMPLE 1

2'-O,(3',9a)-di-N-tris(benzyloxycarbonyl)-N-demethyl-9-deoxo-9a-aza-9a-homoerythromycin A (IIB)

Method 1

To a solution of 9-deoxo-9a-aza-9a-homoerythromycin A (IIA) (10 g) in benzene (50 ml), $NaHCO_3$ (20 g) was added and, then, stepwise, for 2 hours under stirring and heating of the reaction mixture at 60° C., benzyl chloroformate (25 ml) was added drop by drop. The reaction mixture was stirred at the same temperature for further 3 hours and allowed to stand overnight. The benzene suspension was extracted with 0.25N HCl (50 ml); it was then evaporated under reduced pressure to an oily residue and dissolved in $CHCl_3$ (100 ml). The chloroform solution was washed with saturated NaCl (50 ml) and water (50 ml), dried over $K_2CO_3$ and evaporated under reduced pressure. The product obtained was re-precipitated from $Et_2O$-petrol ether (10 ml/100 ml) to give the title product (10.93 g; 70.1%).

m.p. 144°–148° C.; TLC, $CH_2Cl_2$—$CH_3OH$-conc. $NH_4OH$ (90:9:0.5) Rf 0.724; IR ($CHCl_3$) $cm^{-1}$ 3400, 2980, 1750, 1690, 1265; $^1H$ NMR (300 MHz, $CDCl_3$)$\delta$2.76 and 2.82 (3H, 3'—$NCH_3$), 3.37 (3H, 3''—$OCH_3$), 3.48 (1H, H-2'), 7.28 (15H, Ph); $^{13}C$ NMR (75.46 Hz, $CDCl_3$)$\delta$176.78 (C-1), 157.4 (9a-carbamate C=O), 156.5 and 156.1 (3'-carbamate C=O), 154.5 (2'-carbonate C=O), 100.1 (C-1'), 95.8 (C-1''), 55.0 (C-10), 49.5 (3''—$OCH_3$), 35.7 (C-2''), 34.9 (3'—$NCH_3$), 28.7 (C-8); EI-MS m/e 988 ($M^+$-$CO_2CH_2Ph$).

Method 2

To a solution of 9-deoxo-9a-aza-9a-homoerythromycin A (IIA) (5 g) in toluene (30 ml), $NaHCO_3$ (10 g) was added and then benzyl chloroformate (12.5 ml) was added stepwise for 2 hours at room temperature. The reaction mixture was stirred at the same temperature for further 72 hours and it was isolated according to the process disclosed in Method 1 to afford 6.1 g of a crude product. The chromatography of 2.2 g of the obtained mixture on a silica gel column (220 g, Silica gel 60, Merck, 70-230 mesh) using the solvent system $CH_2Cl_2$—$CH_3OH$-conc. $NH_4OH$ (90:9:5) and the concentration of the fractions having Rf 0.724 gave 2'-O,(3',9a)-di-N-tris(benzyloxycarbonyl) derivative (1.3 g) with physical constants disclosed in Method 1.

EXAMPLE 2

O-methylation of 2'-O,(3',9a)-di-N-tris(benzyloxycarbonyl)-N-demethyl-9-deoxo-9a-aza-9a-homoerythromycin A (IA, IB, IC)

To a solution of tris-protected product from Example 1 (6.0 g), methyl iodide (2.3 ml) and 55–60% NaH (dispersion in oil) were added stepwise for 2 hours under stirring at the temperature of 0°–5° C. The reaction mixture was stirred for 1 hour at the same temperature, it was poured onto saturated aqueous $NaHCO_3$ solution (25 ml) and it was extracted with ethyl acetate (75 ml). The combined organic extracts were washed with saturated NaCl (25 ml), dried over $K_2CO_3$ and evaporated at reduced pressure. The obtained product was dissolved in $CHCl_3$ (30 ml), washed with saturated $NaHCO_3$, dried ($K_2CO_3$) and evaporated in vacuo to give 4.06 g of amorphous precipitate. The obtained mixture was subjected to hydrogenolysis according to a process disclosed in Example 3 or, alternatively, to separation on a silica gel column (Silica gel 60, Merck, 70-230 mesh) using the solvent system $CH_2Cl_2$—$CH_3OH$-conc. $NH_4OH$ (90:9:1.5). From 1.0 g of the crude product, by concentration and evaporation of the fractions, according to the rate of eluting the substances from the column, there were successively obtained 2'-O,3'-N-bis(benzyloxycarbonyl)-N-demethyl-6,4''-di-O-methyl-9-deoxo-9a-aza-11-deoxy-9a-homoerythromycin A 9a,11-cyclic carbamate (IA) (158 mg), 2'-O,3'-N-bis(benzyloxycarbonyl)-N-demethyl-6-O-methyl-9-deoxo-9a-aza-11-deoxy-9a-homoerythromycin A 9a,11-cyclic carbamate (IB) (445 mg) and 2'-O,3'-N-bis(benzyloxycarbonyl)-N-demethyl-9-deoxo-9a-aza-11-deoxy-9a-homoerythromycin A 9a,11-cyclic carbamate (IC) (105 mg).

Physical data for the reaction products are as follows:

Substance (IA): TLC, $CH_2Cl_2$—$CH_3OH$-conc. $NH_4OH$ (90:9:1.5) Rf 0.793; IR (KBr)cm$^{-1}$ 3480, 2985, 1465, 1425, 1390, 1260, 1165, 1080, 1010; $^1$H-t NMR (300 MHz, $CDCl_3$)δ2.88, 2.85 (3H, 3'—$NCH_3$), 3.31 (3H, 3''—$OCH_3$), 3.45 (3H, 6—$OCH_3$), 3.53 (3H, 4''—$OCH_3$), 4.43 (1H, H-1'), 4.90 (1H, H-1'').

Substance (IB): TLC, Rf 0.648; IR ($CHCl_3$) cm$^{-1}$ 3480, 2970, 1750, 1710, 1460, 1420, 1385, 1260, 1170, 1120, 1055, 1000; $^1$H NMR (300 MHz, $CDCl_3$)δ2.82, 2.85 (3H, 3''—$NCH_3$), 3.35 (3H, 3''—$OCH_3$), 3.44 (3H, 6—$OCH_3$), 3.49 (1H, H-2'); $^{13}$C NMR (75 MHz, $CDCl_3$)δ174.1 (C-1), 156.3 (3'-carbamate C=O), 155.9 (9a,11 C=O), 154.5 (2'-carbonate C=O), 99.7 (C-1'), 95.8 (C-1''), 57.4 (C-10), 54.3 (6—$OCH_3$), 52.7 (C-9), 49.5 (3''—$OCH_3$); EI-MS m/z 1002 (M+).

Substance (IC): TLC, Rf 0.490; IR (KBr) cm$^{-1}$ 3485, 2980, 1750, 1705, 1460, 1425, 1380, 1260, 1165, 1130, 1060, 995; $^1$H NMR (300 MHz, $CDCl_3$)δ2.81, 2.84 (3H, 3'—$NCH_3$), 3.35 (3H, 3''—$OCH_3$).

EXAMPLE 3

Synthesis of
3'-N-demethyl-6,4''-di-O-methyl-9-deoxo-9a-aza-11-deoxy-9a-homoerythromycin A 9a,11-cyclic carbamate (ID),
3'-N-demethyl-6-O-methyl-9-deoxo-9a-aza-11-deoxy-9a-homoerythromycin A 9a,11-cyclic carbamate (IE) and
3'-N-demethyl-9-deoxo-9a-aza-11-deoxy-9a-homoerythromycin A 9a,11-cyclic carbamate (IF)

To a solution of 4.79 g of the crude product from Example 2 in EtOH (50 ml), NaOAc/HOAc buffer (20 ml of water, 0.6 ml of HOAc and 0.97 g of NaOAc) and Pd/C 10% (2.0 g) were added and the reaction mixture was hydrogenated for 5 hours under stirring in an autoclave at the hydrogen pressure of 5 bar. The catalyst was filtered off. The filtrate was then evaporated at reduced pressure to a thick syrup and dissolved in $CHCl_3$ (50 ml). To the reaction mixture water (50 ml) was added. The pH was then adjusted to 9.5 with 20% NaOH. Next, the layers were separated and the aqueous one was extracted two more times with $CHCl_3$. The combined organic extracts were dried over $K_2CO_3$ and evaporated at reduced pressure to give 3.2 g of a crude product. The crude product was then subjected to reductive N-methylation as disclosed in Example 5 or, alternatively, to chromatography on a silica gel column (Silica gel 60, Merck, 70-230 mesh) using the solvent system $CH_2Cl_2$—$CH_3OH$-conc.$NH_4OH$ (90:9:0.5). From 0.8 g of the crude product, after evaporation of the fractions, according to the rate of elution of the substances from the column, there were isolated 3'-N-demethyl-6,4''-di-O-methyl-9-deoxo-9a-aza-11-deoxy-9a-homoerythromycin A 9a,11-cyclic carbamate (ID) (126 mg), 3'-N-demethyl-6-O-methyl-9-deoxo-9a-aza-11-deoxy-9a-homoerythromycin A 9a,11-cyclic carbamate (IE) (390 mg) and 3'-N-demethyl-9-deoxo-9a-aza-11-deoxy-9a-homoerythromycin A 9a,11-cyclic carbamate (IF) (92 mg).

Physical data for the reaction products are as follows:

Substance (ID):
m.p. 139°–143° C. TLC, $CH_2Cl_2$—$CH_3OH$-conc. $NH_4OH$ (90:9:0.5) Rf 0.310; IR ($CHCl_3$)cm$^{-1}$ 3480, 2985, 1750, 1465, 1420, 1390, 1165, 1085, 1015, 920; $^1$H NMR (300 MHz, $CDCl_3$)δ2.54 (3H, 3'—$NCH_3$), 3.33 (3H, 3''—$OCH_3$), 3.46 (3H, 6—$OCH_3$), 3.53 (3H, 4''—$OCH_3$), 3.65 (1H, H-5'), 4.15 (1H, H-5''), 4.49 (1H, H-1'), 4.88 (1H, H-1''), 5.46 (1H, H-13); EI-MS m/z 773 (M+).

Substance (IE):
m.p. 142°–146° C.; TLC, Rf 0.269; IR ($CHCl_3$) cm$^{-1}$ 3480, 2980, 1745, 1460, 1420, 1385, 1250, 1165, 1070, 1000; $^1$H NMR (300 MHz, $CDCl_3$)δ2.43 (3H, 3'—$NCH_3$), 3.29 (3H, 3''—$OCH_3$), 3.45 (3H, 6—$OCH_3$), 3.61 (1H, H-5), 3.63 (1H, H-5'), 4.12 (1H,H-3), 4.16 (1H, H-5''), 4.37 (1H, H-1'), 4.90 (1H, H-1''), 5.48 (1H, H-13) $^{13}$C NMR (75 MHz, $CDCl_3$)δ174.1 (C-1), 156.9 (9a,11 C=O), 103.4 (C-1'), 96.8 (C-1''), 85.9 (C-5), 80.6 (C-11), 80.0 (C-3); 57.9 (C-10), 53.0 (6—$OCH_3$), 49.7 (C-9), 33.2 (3'—$NCH_3$), 26.7 (6—$CH_3$), 26.1 (C-8); EI-MS m/z 759 (M+).

Substance (IF):
m.p. 155°–158° C.; TLC, Rf 0.172; IR ($CHCl_3$) cm$^{-1}$ 3480, 2980, 1750, 1455, 1420, 1385, 1170, 1080, 1005; $^1$H NMR (300 MHz, $CDCl_3$)δ2.42 (3H, 3'—$NCH_3$), 3.28 (3H, 3''—$OCH_3$), 3.56 (1H, H-5'), 3.60 (1H, H-5), 4.08 (1H, H-3), 4.10 (1H, H-5''), 3.35 (1H, H-1'), 4.89 (1H, H-1''), 5.08 (1H, H-13); $^{13}$C NMR (75 MHz, $CDCl_3$)δ174.3 (C-1), 156.5 (9a,11C=O), 103.3 (C-1'), 96.7 (C-1''), 85.7 (C-5), 80.8 (C-11), 78.7 (C-3); 58.3 (C-10), 49.7 (C-9), 33.1 (3'—$NCH_3$), 26.9 (6—$CH_3$), 25.8 (C-8); EI-MS m/z 745 (M+).

EXAMPLE 4

3'-N,demethyl-6-O-methyl-9-deoxo-9a-aza-11-deoxy-9a-homoerythromycin A 9a,11-cyclic carbamate (IE)

To a solution of the substance (IB) (345 mg) from Example 2 in MeOH (20 ml), water (5 ml) containing HOAc (0.15 ml) and NaOAc (0.25 g) as well as Pd/C 5% (0.5 g) were added. Then, the reaction mixture was hydrogenated under stirring in an autoclave at 20 bar for 30 minutes. Next, the catalyst was filtered off and the product was isolated according to the process disclosed in Example 3 to give the substance (IE) (210 mg) having the physical constants as disclosed in the previous Example.

EXAMPLE 5

Synthesis of
6,4''-di-O-methyl-9-deoxo-9a-aza-11-deoxy-9a-homoerythromycin A 9a,11-cyclic carbamate (IG),
6-O-methyl-9-deoxo-9a-aza-11-deoxy-9a-homoerythromycin A 9a,11-cyclic carbamate (IH) and
9-deoxo-9a-aza-11-deoxy-9a-homoerythromycin A 9a,11-cyclic carbamate (IJ)

To a solution of a crude product (2.2 g) from Example 3 in $CHCl_3$ (50 ml), 37% formaldehyde (0.57 ml) and 98% formic acid (0.52 ml) were added. Subsequently, the reaction mixture was stirred for 8 hours at the reflux temperature. After cooling to room temperature, the reaction mixture was poured onto water (40 ml). Next $CHCl_3$ (20 ml) was added, the pH was adjusted with 20% NaOH to 9.0. Subsequently, the chloroform layer was separated and the aqueous layer was extracted two more times with $CHCl_3$ (30 ml). The combined organic extracts were dried over $K_2CO_3$ and evaporated under reduced pressure to give a crude product (2.2 g). The crude product was then subjected to chromatography on a silica gel column. Using the solvent system $CH_2Cl_2$—$CH_3OH$-conc. $NH_4OH$ (90:9:0.5), by elution and concentration of the corresponding fractions, there were isolated 6,4''-di-O-methyl- 9-deoxo-9a-aza-11-deoxy-9a-homoerythromycin A 9a,11-cyclic carbamate (IG) (210 mg), 6-O-methyl-9-deoxo-9a-aza-11-deoxy-9a-homoerythromycin A 9a,11-cyclic carbamate (IH) (876 mg) and 9-deoxo-9a-aza-11-deoxy-9a-homoerythromycin A 9a,11-cyclic carbamate (IJ) (160 mg).

Physical data for the reaction products are as follows :

Substance (IG):
m.p. 127°–131° C.; TLC, EtOAc-(n-hexane)-$Et_2NH$ (100:100:20) Rf 0.645; IR ($CHCl_3$)$cm^{-1}$ 3480, 2980, 1755, 1465, 1420, 1390, 1170, 1100, 1060; $^1H$ NMR (300 MHz, $CDCl_3$)δ2.28 (6H, 3'—$N(CH_3)_2$), 2.68 (1H, H-4'), 3.31 (3H, 3''—$OCH_3$), 3.45 (3H, 6—$OCH_3$), 3.54 (3H, 4''—$OCH_3$), 3.65 (1H, H-5'), 4.22 (1H, H-5''), 4.43 (1H, H-11), 4.45 (1H, H-1'), 4.88 (1H, H-1''), 5.45 (1H, H-13); $^{13}C$ NMR (75 MHz, $CDCl_3$)δ174.3 (C-1), 156.8 (9a,11 C=O), 102.5 (C-1'), 96.6 (C-1'), 88.9 (C-4''), 83.1 (C-5), 79.5 (C-11), 62.1 (4''—$OCH_3$), 57.6 (C-10), 58.0 (6—$OCH_3$), 49.7 (C-9), 40.2 (3'—$N(CH_3)_2$), 26.3 (C-8), 26.2 (6—$CH_3$); EI-MS m/z 787 ($M^+$).

Substance (IH):
m.p. 135°–138° C.; TLC, Rf 0,546; IR ($CHCl_3$) $cm^{-1}$ 3480, 2980, 1755, 1465, 1420, 1390, 1170, 1100, 1060; $^1H$ NMR (300 MHz, $CDCl_3$)δ2.30 (6H, 3'—$N(CH_3)_2$), 3.31 (3H, 3''—$OCH_3$), 3.35 (3H, 6—$OCH_3$), 3.65 (1H, H-10), 4.32 (1H, H-11), 4.42 (1H, H-1'), 4.91 (1H, H-1'), 5.46 (1H, H-13); $^{13}C$ NMR (75 MHz, $CDCl_3$)δ174.4 (C-1), 156.7 (9a,11 C=O), 103.2 (C-1'), 96.5 (C-1'), 84.1 (C-5), 80.1 (C-3), 79.8 (C-11), 77.9 (C-4''), 57.6 (C-10), 52.9 (6—$OCH_3$), 49.6 (C-9), 49.4 (3''—$OCH_3$), 40.3 (3'—$N(CH_3)_2$), 26.8 (6—$CH_3$), 26.1 (C-8): EI-MS m/z 773 ($M^+$).

Substance (IJ):
m.p. 133°–136° C.; TLC, Rf 0.454; IR ($CHCl_3$) $cm^{-1}$ 3475, 2980, 1750, 1460, 1420, 1385, 1260, 1220, 1100, 1050; $^1H$ NMR (300 MHz, $CDCl_3$)δ2.29 (6H, 3'—$N(CH_3)_2$), 3.32 (3H, 3''—$OCH_3$), 3.53 (1H, H-5'), 4.02 (1H, H-5''); $^{13}C$ NMR (75 MHz, $CDCl_3$):δ174.2 (C-1), 156.4 (9a,11 C=O), 103.4 (C-1'), 96.6 (C-1''), 49.5 (3''—$OCH_3$), 40.3 (3'—$N(CH_3)_2$); EI-MS m/z 759($M^+$).

EXAMPLE 6

6-O-methyl-9-deoxo-9a-aza-11-deoxy-9a-homoerythromycin A 9a,11-cyclic carbamate (IH)

To a solution of substance (IE) (0.48 g) in acetone (20 ml), 37% formaldehyde (0.1 ml) and 98% formic acid (0.07 ml) were added. Then, the reaction mixture was stirred for 6 hours at reflux temperature. After allowing the reaction mixture to stand overnight at room temperature, acetone was evaporated at reduced pressure. Next, water (30 ml) and $CHCl_3$ (20 ml) were added. Then, the reaction mixture was extracted twice with $CHCl_3$ (20 ml). After drying the combined chloroform extracts over $K_2CO_3$ and evaporating $CHCl_3$ in vacuo, 6-O-methyl derivative (IH) (0.4 g) having the physical constants as disclosed in Example 5 was obtained.

We claim:

1. A 9-deoxo-9a-aza-11-deoxy-9a-homoerythromycin A 9a,11-cyclic carbamates of the formula (I)

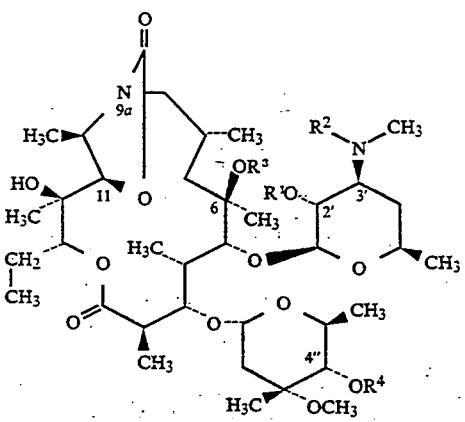

wherein

| | |
|---|---|
| $R^1=R^2=CO_2CH_2C_6H_5$, $R^3=R^4=CH_3$, | (IA) |
| $R^1=R^2=CO_2CH_2C_6H_5$, $R^3=CH_3$, $R^4=H$, | (IB) |
| $R^1=R^2=CO_2CH_2C_6H_5$, $R^3=R^4=H$, | (IC) |
| $R^1=R^2=H$, $R^3=R^4=CH_3$, | (ID) |
| $R^1=R^2=R^4=H$, $R^3=CH_3$, | (IE) |
| $R^1=R^2=R^3=R^4=H$, | (IF) |
| $R^1=H$, $R^2=R^3=R^4=CH_3$, | (IG) |
| $R^1=R^4=H$, $R^2=R^3=CH_3$, | (IH) |
| $R^1=R^3=R^4=H$, $R^2=CH_3$, | (IJ) | or pharmaceutically acceptable addition salts thereof with inorganic or organic acids.

2. Compound according to claim 1, characterized in that $R^1$ and $R^2$ are the same and have the meaning of a benzyloxycarbonyl group and $R^3$ and $R^4$ have the meaning of methyl.

3. Compound according to claim 1, characterized in that $R^1$ and $R^2$ are the same and have the meaning of a benzyloxycarbonyl group, $R^3$ is methyl and $R^4$ has the meaning of hydrogen.

4. Compound according to claim 1, characterized in that $R^1$ and $R^2$ are the same and have the meaning of a benzyloxycarbonyl group, and $R^3$ and $R^4$ have the meaning of hydrogen.

5. Compound according to claim 1, characterized in that $R^1$ and $R^2$ are the same and have the meaning of hydrogen, and $R^3$ and $R^4$ have the meaning of a methyl group.

6. Compound according to claim 1, characterized in that $R^1$, $R^2$ and $R^4$ are the same and have the meaning of hydrogen, and $R^3$ is a methyl group.

7. Compound according to claim 1, characterized in that $R^1$, $R^2$, $R^3$ and $R^4$ are the same and have the meaning of hydrogen.

8. Compound according to claim 1, characterized in that $R^1$ is hydrogen, whereas $R^2$, $R^3$ and $R^4$ are the same and have the meaning of a methyl group.

9. Compound according to claim 1, characterized in that $R^1$ and $R^4$ are the same and have the meaning of hydrogen and $R^2$ and $R^3$ have the meaning of a methyl group.

10. Compound according to claim 1, characterized in that $R^1$, $R^3$ and $R^4$ are the same and have the meaning of hydrogen, and $R^2$ is a methyl group.

11. Compound of the formula (II)

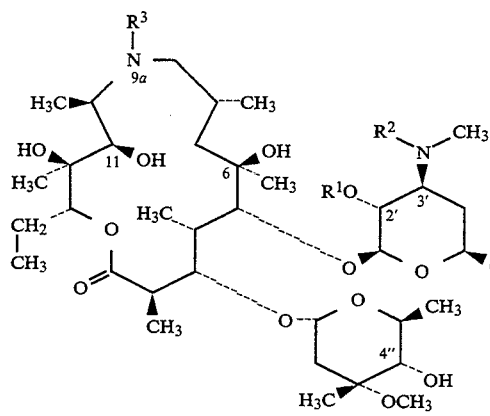

wherein

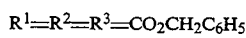
$$R^1=R^2=R^3=CO_2CH_2C_6H_5 \quad (IIB).$$

12. Process for preparing 9-deoxo-9a-aza-11-deoxy-9a-homoerythromycin A 9a,11-cyclic carbamates of the formula (I)

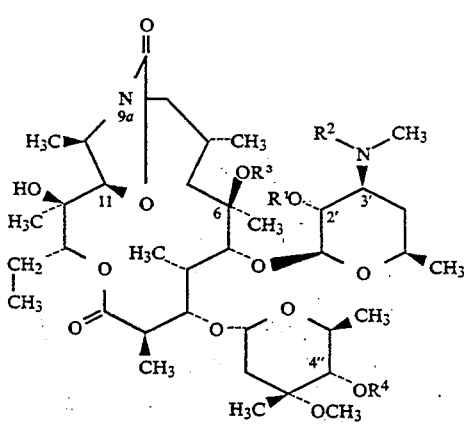

wherein

| | |
|---|---|
| $R^1=R^2=CO_2CH_2C_6H_5, R^3=R^4=CH_3,$ | (IA) |
| $R^1=R^2=CO_2CH_2C_6H_5, R^3=CH_3, R^4=H,$ | (IB) |
| $R^1=R^2=CO_2CH_2C_6H_5, R^3=R^4=H,$ | (IC) |
| $R^1=R^2=H, R^3=R^4=CH_3,$ | (ID) |
| $R^1=R^2=R^4=H, R^3=CH_3,$ | (IE) |
| $R^1=R^2=R^3=R^4=H$ | (IF) |
| $R^1=H, R^2=R^3=R^4=CH_3,$ | (IG) |
| $R^1=R^4=H, R^2=R^3=CH_3,$ | (IH) |
| $R^1=R^3=R^4=H, R^2=CH_3,$ | (IJ) | characterized in that 9-deoxo-9a-aza-9a-homoerythromycin A of the formula (II)

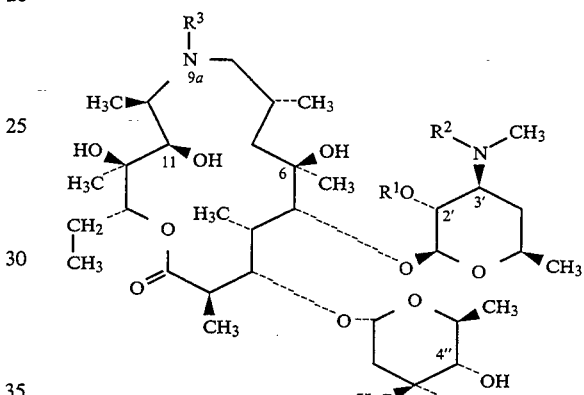

wherein $$R^1=R^3=H, R^2=CH_3, \quad (IIA)$$

is subjected to a reaction with benzyl chloroformate in the presence of $NaHCO_3$, in a solvent inert under the reaction conditions, at a temperature from room temperature to the reflux temperature of the reaction mixture for 3 hours to 3 days to obtain a 2'-O,(3',9a)-di-N-tris(benzyloxycarbonyl)-N-demethyl-9-deoxo-9a-aza-9a-homoerythromycin A of the formula (II) wherein $$R^1=R^2=R^3=CO_2CH_2C_6H_5, \quad (IIB)$$

which is then subjected to O-methylation with 1 to 8 equivalents of a methylating agent in the presence of at least one base, in a polar aprotic solvent at a temperature from 0° C. to room temperature for 1 to 24 hours to obtain a mixture of 9-deoxo-9a-aza-11-deoxy-9a-homoerythromycin A 9a,11-cyclic carbamates of the formula (I) wherein

| | |
|---|---|
| $R^1=R^2=CO_2CH_2C_6H_5, R^3=R^4=CH_3,$ | (IA) |
| $R^1=R^2=CO_2CH_2C_6H_5, R^3=CH_3, R^4=H,$ | (IB) |
| $R^1=R^2=CO_2CH_2C_6H_5, R^3=R^4=H,$ | (IC) | which, if necessary, are subjected to
A) chromatography on a silica gel column to give chromatographically homogenous substances (IA)–(IC), which are then subjected to elimination of the protective benzyloxycarbonyl groups in 2'- and 3'-positions by a hydrogenolysis process in a solution of a lower alcohol, in the presence of NaOAc/HOAc buffer (pH 5) and a catalyst, in the hydrogen atmosphere at a pressure of 1 to 20 bar under stirring at room temperature for 30 minutes to 10 hours to give 9-deoxo-9a-aza-11-deoxy-9a-homoerythromycin A 9a,11-cyclic carbamates of the formula (I) wherein

 (ID)

 (IE)

 (IF)

which are then subjected to reductive N-methylation with 1 to 3 equivalents of formaldehyde (37%) and with the same or a 2-fold amount of formic acid (98–100%) in a solvent inert under reaction conditions, at the reflux temperature of the reaction mixture, from 2 to 8 hours to give 9-deoxo-9a-aza-11-deoxy-9a-homoerythromycin A 9a,11-cyclic carbamates of the formula (I) wherein

 (IG)

 (IH)

 (IJ)

or alternatively,

B) elimination of protective benzyloxycarbonyl groups in 2'- and 3'-positions by a hydrogenolysis process and then to reductive N-methylation of 3'-methylamino group according to a method disclosed under A) to give a mixture of 9-deoxo-9a-aza-11-deoxy-9a-homoerythromycin A 9a,11-cyclic carbamates of the formula (I) wherein

 (IG)

 (IH)

 (IJ)

which is subjected to a separation on a silica gel column to give chromatographically homogenous products (IG)–(IJ), which are then, if necessary, subjected to the reaction with at least one equivalent of inorganic or organic acids to give the corresponding pharmaceutically acceptable addition salts with inorganic or organic acids.

13. A process according to claim 12, wherein said solvent that said reaction with benzyl chloroform is carried out in is selected from the group consisting of benzene and toluene.

14. A process according to claim 12, wherein said base that said O-methylation is carried out in the presence of includes at least one member selected from the group consisting of alkali metal hydrides, hydroxides, and organic bases.

15. A process according to claim 14, wherein said base is selected from the group consisting of sodium hydroxide, potassium hydroxide, and n-BuLi.

16. A process according to claim 12, wherein said polar aprotic solvent that said O-methylation is carried out in is selected from the group consisting of dimethyl sulfoxide and N,N-dimethylformamide.

17. A process according to claim 16, wherein said solvent further includes at least one solvent that is inert under reaction conditions.

18. A process according to claim 17, wherein said solvent that is inert under reaction conditions is tetrahydrofuran.

19. A process according to claim 12, wherein said solvent that said reductive N-methylation is carried out in is inert under reaction conditions.

20. A process according to claim 19, wherein said solvent includes at least one member of the group consisting of halogenated hydrocarbons, alcohols, and lower ketones.

21. A process according to claim 20, wherein said solvent is selected from the group consisting of chloroform, ethanol, and acetone.

22. A process according to claim 12, wherein said catalyst that said hydrogenolysis is carried out in the presence of is selected from the group consisting of palladium black or palladium on carbon.

23. A process according to claim 12, wherein said lower alcohol is ethanol.

24. Pharmaceutical composition comprising a pharmaceutically acceptable carrier and an antibacterially effective amount of the compounds as claimed in claim 1.

25. Pharmaceutical composition comprising a pharmaceutically acceptable carrier and an antibacterially effective amount of the compound as claimed in claim 11.

26. A method of treating bacterial infections, said method comprising the step of administering to a patient in need thereof an antibacterially effective amount of a 9-deoxo-9a-aza-11-deoxy-9a-homoerythromycin A 9a,11-cyclic carbamates of the formula (I)

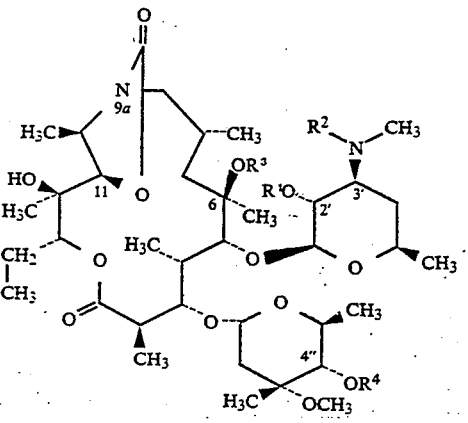

wherein

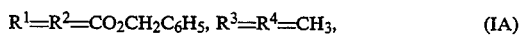 (IA)

 IB)

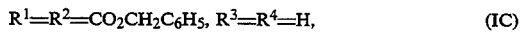 (IC)

 (ID)

 (IE)

 (IF)

 (IG)

 (IH)

 (IJ)

or pharmaceutically acceptable addition salts thereof with inorganic or organic acids.

* * * * *